US010865334B2

(12) United States Patent
van Spronsen et al.

(10) Patent No.: US 10,865,334 B2
(45) Date of Patent: *Dec. 15, 2020

(54) PROCESS FOR EXTRACTING MATERIALS FROM BIOLOGICAL MATERIAL

(71) Applicant: Universiteit Leiden, Leiden (NL)

(72) Inventors: Jacob van Spronsen, Noordwijk (NL); Geert-Jan Witkamp, Bergschenhoek (NL); Frank Hollman, The Hague (NL); Young Hae Choi, Leiden (NL); Robert Verpoorte, Leiden (NL)

(73) Assignee: Universiteit Leiden, Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/451,845

(22) Filed: Aug. 5, 2014

(65) Prior Publication Data

US 2014/0341934 A1   Nov. 20, 2014

Related U.S. Application Data

(63) Continuation of application No. 13/702,633, filed as application No. PCT/NL2011/050407 on Jun. 7, 2011.

(30) Foreign Application Priority Data

Jun. 7, 2010 (NL) ..................................... 2004835

(51) Int. Cl.
| C09K 3/00 | (2006.01) |
| B01D 11/02 | (2006.01) |
| B01D 11/04 | (2006.01) |
| C07D 311/62 | (2006.01) |
| C07H 17/07 | (2006.01) |

(52) U.S. Cl.
CPC ............ *C09K 3/00* (2013.01); *B01D 11/0288* (2013.01); *B01D 11/04* (2013.01); *C07D 311/62* (2013.01); *C07H 17/07* (2013.01)

(58) Field of Classification Search
None
See application file for complete search history.

(56) References Cited

U.S. PATENT DOCUMENTS

| 9,441,146 B2 * | 9/2016 | van Spronsen .... B01D 11/0288 |
| 2004/0097755 A1 * | 5/2004 | Abbott ................... B01J 31/006 562/553 |
| 2004/0262578 A1 | 12/2004 | Wasserscheid et al. |
| 2007/0215300 A1 | 9/2007 | Upfal et al. |
| 2009/0117628 A1 * | 5/2009 | Gorke ....................... C12P 7/62 435/129 |
| 2009/0156676 A1 | 6/2009 | Molino et al. |
| 2010/0120673 A1 | 5/2010 | Yoong et al. |

FOREIGN PATENT DOCUMENTS

| JP | 2004350554 A | 12/2004 |
| JP | 2008-535483 A | 9/2008 |
| WO | 2006116126 | 11/2006 |
| WO | 2009120839 | 10/2009 |

OTHER PUBLICATIONS

Verpoorte R "Natural Products Research: Quo Vaids?" www.fapesp.br/eventos/2014/12/biota/verpoorte.pdf. Published Jan. 27, 2009.*
Cruz et al. "Dynamic mechanical thermal analysis of aqueous sugar solutions containing fructose, glucose, sucrose, maltose and lactose" Intl. J. Food Sci. & Tech. 36:539-550. (Year: 2001).*
Hayyan et al. "A novel technique for separating glycerine from palm oil-based biodiesel using ionic liquids", Fuel Processing Technology, Sep. 26, 2009, No. 91, pp. 116-120.
Tang et al. "Functional amino acid ionic liquids as solvent and selector in chiral extraction", Journal of Chromatography A, May 19, 2010, No. 1217, pp. 4669-4674.
Chiappe, "The Possibility to obtain a new generation of ionic liquids starting from natural compounds" Green Chemical Reactions, NATO Science For Peace And Security Series, vol. 2008, Dec. 31, 2008, pp. 13-35.
Wang et al., "New progress in biocatalysis and biotransformation of flavonoids", Journal of Medicinal Plants Research, vol. 4, No. 10, May 18, 2010, pp. 847-856.
Chandrasekaran SK and Judson King C, Solid-Liquid Phase Equilibria in Multicomponent Aqueous Sugar Solutions, J. Food Sic, 36 :699-704, Published 1971.
Choi, Y.H. et al., Are Natural Deep Eutectic Solvents the Missing Link in Understanding Cellular Meatbolism and Physiology?, Plant Physiology, Aug. 2011, vol. 156, pp. 1701-1705.
Cruz et al., Dynamic mechanical thermal analysis of aqueous sugar solutions containing fructose, glucose, sucrose, maltose and lactose, Int.l J. Food Sci. And Tech, 6 :539-550, Published 2001.
Dai, Y. et al., Application of natural deep eutectic solvents to the extraction of anthocyanins from Catharanthus roseus with high extractability and stability replacing conventional organic solvents, Journal of Chromatography A, 2016, 1434:50-56.
Dai, Y. et al., Ionic Liquids and Deep Eutectic Solvents in Natural Products Research: Mixtures of Solids as Extraction Solids, Journal of Natural Products, 2013, 67(11):2162-2173.
Dai, Y. et al., Natural deep eutectic solvents providing enhanced stability of natural colorants from safflower (Carthamus tinctorius), Food Chemistry, 2014, 156:116-121.
Dai, Y. et al., Tailoring properties of natural deep eutectic solvents with water to facilitate their applications, Food Chemistry, 2015, 187:14-19.

(Continued)

Primary Examiner — Larry D Riggs, II
Assistant Examiner — Zachary J Miknis
(74) Attorney, Agent, or Firm — Banner & Witcoff, Ltd.

(57) ABSTRACT

The invention is directed to a process for extracting materials from biological material, which process is characterized in that the naturally occurring biological material is treated with an extractant consisting of a deep eutectic solvent of natural origin or a an ionic liquid of natural origin to produce a biological extract of natural origin dissolved in the said solvent or ionic liquid.

8 Claims, No Drawings

(56) References Cited

OTHER PUBLICATIONS

Gallegos-Infante et al., Glass Transition Temperature Behavior of a Model Blend of Carbohydrates, Ciencia y Tecnologia Alimentari 5 :6-10, Published 2005.

Gutierrez et al. "Freeze-Drying of Aqueous Solutions of Deep Eutectic Solvents: A Suitable Approach to Deep Eutectic Suspensions of Self-Assembled Structures" Langmuir 25: 5509-5515, 2009.

* cited by examiner

PROCESS FOR EXTRACTING MATERIALS FROM BIOLOGICAL MATERIAL

This application is a Continuation of U.S. application Ser. No. 13/702,633 filed Feb. 18, 2013 which is the United States national stage of International Application No. PCT/NL2011/050407, filed Jun. 7, 2011, which was published under PCT Article 21 in English as International Publication No. WO 2011/155829, and which claims benefit of Netherlands Patent Application No. 2004835 filed Jun. 7, 2010 which is herein incorporated by reference.

The present invention is directed to a process for extracting materials from biological materials.

Drugs, flavors, fragrances, agrochemicals, dyes etc., both from synthetic and natural sources are often poorly soluble in water. Therefore extraction, purification, administration requires the use of less polar solvents, such as alcohols, acetone, ethyl acetate, chloroform etc. Such solvents present several problems such as: toxicity for the producer/patient/consumer, environmental problems, explosions and the like.

Ionic liquids can be environmentally benign and safe replacements for the traditional volatile organic solvents in various chemical processes. The reason that ionic liquids are considered to be 'green' solvents is their negligible vapor pressure. However, ionic liquids can have a hidden environmental cost because they are synthesized from petrochemical resources. In a lot of synthesis routes halogen atoms are involved. Halogen materials in ionic liquids are undesirable, because of the low hydrolysis stability, the high toxicity, the low biodegradability and the high disposal cost. For example, fluorinated anions such as $PF_6^-$ and $BF_4^-$ are sensitive to water and may release the corrosive and toxic hydrogen fluoride. Moreover, the alkyl halides used in the syntheses of many ionic liquids are greenhouse gases and ozone-depleting materials.

The reason that ionic liquids are also considered to be safe solvents is because their lack of volatility greatly reduces any chance of exposure other than by direct physical contact with skin or by ingestion. However, most conventional ionic liquids are irritating and have a toxicity comparable to common organic solvents. From biological tests it appeared that the toxicity of ionic liquids is mainly determined by the type of cation and that ionic liquids with short alkyl substituents in the cation usually have a lower toxicity.

A solution to the problems mentioned above is the development of halogen-free ionic liquids, such as ionic liquids with the alkyl sulfate, the alkyl carbonate and the sulfonate anion. It was also found that some ionic liquids with ester groups in their alkyl side chains are biodegradable. However, these ionic liquids are still synthesized using petrochemical resources.

In WO2006/116126 a process is described for extracting biopolymers from biomass, using ionic liquids. Generally the ionic liquids described therein are of petrochemical nature. The biopolymers extracted are chitin, chitosan, collagen and keratin. Polyhydroxyalkanoate is extracted from genetically engineered plants.

As indicated above, there is a need for an improved process for extracting organic compounds from natural sources, without the need for the use of organic solvents or other synthetic materials.

Further, there is a need for a process that can truly be considered 'green', i.e. using only natural compounds.

The invention is based on the surprising fact that some specific naturally occurring materials can suitably be used for extracting materials from biological sources. These materials are deep eutectic solvents (or mixtures) of natural origin or ionic liquids of natural origin.

Deep eutectic solvents are liquids having a melting point that is much lower than the melting points of the two compounds that form the eutectic mixture. Generally, they are formed between a variety of quaternary ammonium salts and carboxylic acids. The deep eutectic phenomenon was first described in 2003 for a mixture of choline chloride and urea in a 1:2 mole ratio, respectively. Other deep eutectic solvents of choline chloride are formed with phenol and glycerol. Deep eutectic solvents are able to dissolve many metal salts like lithium chloride and copper(II)oxide. Also, organic compounds such as benzoic acid and cellulose have great solubility in deep eutectic solvents. Compared to ordinary solvents, eutectic solvents have a very low volatility and are non-flammable. They share a lot of characteristics with ionic liquids, but they are ionic mixtures and not ionic compounds.

Instead, choline citrate is a real ionic liquid. This compound was formed by dissolving citric acid in water, followed by addition of choline hydroxide (in the ratio 2:1) dissolved in methanol. The solvent (water and methanol) was evaporated. The product choline citrate was a slightly yellow viscous liquid, and not a solid. This is probably the first naturally occurring ionic liquid found.

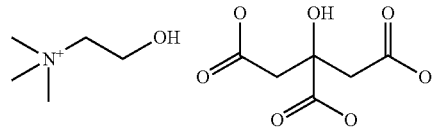

choline citrate

In addition to the ions, sugar-based liquids can be deep eutectic solvents.

According to the invention a process for extracting materials from biological material is provided, which process is characterized in that the naturally occurring biological material is treated with an extractant consisting of a deep eutectic solvent of natural origin or a an ionic liquid of natural origin to produce a biological extract of natural origin dissolved in the said solvent or ionic liquid.

Surprisingly it has been found that deep eutectic solvents of natural origin, as defined herein, and natural ionic liquids are suitable extractants for biological materials. These extractants are very efficient and selective, and as they are of natural origin, they are extremely efficient and suitable for extracting components from biological materials, resulting in an efficient process, providing a good yield. The melting points of the deep eutectic mixtures and ionic liquids is preferable below 25° C. The materials are thus preferably liquid at ambient temperatures.

Suitable deep eutectic solvents to be used in the present invention, i.e. mixtures of materials of natural origin, are based on mixtures of at least two compounds, substantially without chemical or ionic bonding. The first component of the solvents is preferably selected from at least one naturally occurring organic acid or an inorganic compound, such as a salt.

The second component is preferably selected from at least one naturally occurring mono- or dimeric sugar, sugar alcohol, amino acid, di or tri alkanol or choline derivatives, such as choline or phosphatidyl choline.

Said sugar or sugar alcohol may be selected from the group of sucrose, glucose, fructose, lactose, maltose, cellobiose, arabinose, ribose, ribulose, galactose, rhamnose, raffinose, xylose, sucrose, mannose, trehalose, mannitol, sorbitol, inositol, ribitol, galactitol, erythritol, xyletol and adonitol, and, as well as their phosphates.

The said organic acid may be selected from malic acid, maleic acid, citric acid, lactic acid, pyruvic acid, fumaric acid, succinic acid, lactic acid, acetic acid, aconitic acid, tartaric acid, malonic acid, ascorbic acid, glucuronic acid, oxalic acid, neuraminic acid and sialic acids.

In general it is preferred that the ionic liquid or deep eutectic solvent is free of chlorine/chloride.

In certain solvents additionally further components may be present, such as water, phenolics, etc. These additional compounds are generally present in minor amounts, such as below 5 wt. %.

Suitable examples of inorganic compounds are the phosphates, sulfates, sulfites and halogenides, such as $NaH_2PO_4$, $Na_2HPO_4$, $NaHSO_3$, $Na_2SO_4$, $CaCl_2$, $MgCl_2$, KCl, NaCl and KI.

Specific examples of deep eutectic solvents are given in the table below, but also honey, maple syrup, and nectar are examples of deep eutectic solvents that can be used as extraction solvent (which are based on sugar, and small amounts of phenolics and amino acids).

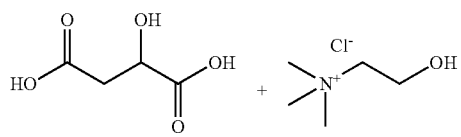

Deep eutectic mixture of malic acid with choline chloride

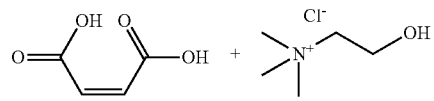

Deep eutectic mixture of maleic acid with choline chloride

Suitable ionic liquids are based on naturally occurring anions selected from the group of malic acid, maleic acid, citric acid, lactic acid, tartaric acid glucosamine, glucuronic acid, neuraminic acid and sialic acids.

The said ionic liquid is further based on naturally occurring cations selected from the group of choline, betaine, betanine, gamma-amino butyric acid, betalaine, acetylcholine, glucosamine, glutamine, glutamate, asparagine, aspartic acid, alanine, lysine, arginine, proline, threonine, putrescine, cadaverine and choline derivatives.

In a more preferred embodiment the said ionic liquid is choline citrate.

The ratio of the components of the deep eutectic solvents and ionic liquids depends on the structure of the two or more constituents of the solvent or liquid.

For deep eutectic solvents quite often the two components are present in an equimolar ratio, although other ratio's have also been observed. Generally however, the molar ratio can be expressed in whole numbers. These ratio's generally vary from 1:1 to 4:1.

Ionic liquids are by definition salts anions and cations and accordingly the ratio is determined by the valence of the ions.

In the following tables 1 and 2 the composition and properties of deep eutectic solvent (des), as well as some solubility data have been given.

TABLE 1

The composition and properties of deep eutectic solvent (des)

| No. | Composition (molar ratio) | $H_2O$ w % | water activity (40° C.) | density (40° C.) g/cm3 | viscosity (40° C.) mm2/s | $E_T(NR)$ | $T_{decom}$/° C. | $T_g$/° C. |
|---|---|---|---|---|---|---|---|---|
| MCH | Ma:Ch:$H_2O$(1:1:2) | 11.62% | 0.195 | 1.246 | 445.9 | 44.81 | 201 | −71.32 |
| GlyCH | Gly:Ch:$H_2O$(2:1:1) | 5.26% | 0.126 | 1.1742 | 51.3 | 49.55 | 187 | −101.59 |
| MAH | Ma:β-Ala:$H_2O$ (1:1:3) | 19.48% | 0.573 | 1.352 | 174.6 | 48.05 | 164 | −70.88 |
| PMH | Pro:Ma:$H_2O$(1:1:3) | 17.81% | 0.591 | 1.3184 | 251 | 48.3 | 156 | −61.29 |
| CaGH8 | CaCl2:Glc:$H_2O$(5/4:1:8) | 31.11% | 0.331 | 1.4904 | 720 | 54.56 | 137 | −61.39 |
| FCH | Fru:Ch:$H_2O$ (1:2.5:2.5) | 7.84% | 0.151 | 1.2078 | 280.8 | 49.81 | 160 | −84.58 |
| XCH | Xyl:Ch:$H_2O$ (1:2:2) | 7.74% | 0.141 | 1.2095 | 308.3 | 49.81 | 178 | −81.8 |
| SCH | Suc:Ch:$H_2O$ (1:4:4) | 7.40% | 0.182 | 1.2269 | 581 | 49.72 | >200 | −82.96 |
| FGSH | Fru:Glc:Suc:$H_2O$ (1:1:1:11) | 18.70% | 0.662 | 1.3657 | 720 | 48.21 | 138 | −50.77 |
| GCH | Glc:Ch:$H_2O$ (1:2.5:2.5) | 7.84% | 0.162 | 1.197 | 397.4 | 49.72 | 170 | −83.86 |
| PdCH | 1,2Prop:Ch:H20 (1:1:1) | 7.70% | 0.242 | 1.0833 | 33.0 | 50.07 | 162 | −109.55 |
| LGH | Lac:Glc:$H_2O$(5:1:2) | 7.89% | 0.496 | 1.2495 | 37.0 | 44.81 | 135 | −77.06 |
| SoCH | So:Ch:$H_2O$(1:2.5; 3) | 11.17% | 0.12 | 1.185385 | 138.4 | 49.98 | >200 | −89.62 |
| XoCH | Xo:Ch:$H_2O$(1:2:3) | 11.17% | 0.116 | 1.17841 | 86.1 | 49.72 | >200 | −93.33 |
| M2 | Ma:Pro:Xo:Ch:H2O(1:1:1:2.5:6) | 12.58% | 0.218 | 1.24729 | | 49.13 | | −84.4 |
| M3 | Ma:Pro:Ch:$H_2O$(1:1:1:4) | 15.62% | 0.213 | 1.18469 | | 49.21 | | −72.96 |

Ala = alanine
Ch = choline
Fru = fructose
Glc = glucose
Gly = glycerol
Lact—lactose
Ma = malic acid
1,2Pro = 1,2-propanediol
Pro = proline
So = sorbitol
Suc = sucrose
Xo = xylitol
Xyl = xylose

TABLE 2

Summary of some solubility data in some typical Des at 40° C. (mg/ml) (n = 3)

| Des | rutin | quercetin | cinnamic acid | carthamin | 1,8-dihydroxy-anthraquinone | paclitaxel | ginkgolide B |
|---|---|---|---|---|---|---|---|
| LGH | 8.14 ± 0.79 | 1.72 ± 0.09 | 13.11 ± 0.38 | 1.24 ± 0.21 | 0.20 ± 0.01 | 5.39 ± 0.55 | 1.93 ± 0.31 |
| GCH | 121.63 ± 1.45 | 20.06 ± 0.41 | 8.64 ± 0.46 | 27.20 ± 0.39 | 0.20 ± 0.04 | 0.83 ± 0.16 | 5.85 ± 0.42 |
| PdCH | 352.90 ± 31.19 | 205.17 ± 7.31 | 58.29 ± 2.79 | 22.47 ± 1.00 | 0.17 ± 0.00 | 11.71 ± 0.68 | 78.42 ± 14.45 |
| SoCH | 149.21 ± 2.61 | 145.84 ± 2.82 | 4.50 ± 0.21 | 14.05 ± 0.66 | 0.08 ± 0.01 | 0.59 ± 0.01 | 1.70 ± 0.01 |
| $H_2O$ | 0.028 ± 0.00 | 0.035 ± 0.003 | 0.57 ± 0.01 | 1.43 ± 0.01 | 0.00 ± 0.00 | 0.01 ± 0.00 | 0.15 ± 0.00 |

The present invention deals with extracting materials from biological products. In the most general scope, all materials of biological origin may be used. Suitable examples are plants, insects, animals or micro-organisms.

From these materials a great variety of products can be isolated using the process of the present invention. More in particular the extracted or dissolved material is a flavonoid (e.g. rutin and quercetin), an anthocyanin, a colorant, an alkaloid, a terpenoid, a phenylpropanoid a glycoside, a phenolic compound, such as cinnamic acid, a ginkgolide, carthamin, an anthraquinone, paclitaxel, taxoid, a lignan, a coumarin, a cinnamic acid derivative, azadirachtin, artimisinin, a hop bitter acid, a cannabinoid, vanillin, a polyketide, a colorant, a flavor, a fragrance, a dye, a biocide or a mixture of any of these compounds. Also proteins (enzymes), toxins, vaccins, DNA, RNA and polysaccharides may be extracted from suitable sources.

In particular, the invention is directed to extracting natural materials from natural sources, i.e. not genetically engineered. In a further preferred embodiment, valuable materials are thus extracted or dissolved, such as non-polymeric compounds, as listed above. Non-polymeric compounds are defined as those compounds that do not consist of three or more repeating units of the same moiety (monomer) or of the same type of monomers, such as amino acids or sugars.

These non-polymeric materials are, for example, suitable intermediates or products suitable in food, pharma, cosmetics and agrochemicals. More in particular it is preferred to extract flavors and fragrance from plant, vanillin from vanilla, capsaicin from *Capsicum*, hop bitter acids from hops, cannabinoids from cannabis, azadirachtin from neem plant material, paclitaxel from *Taxus* plant material, artimisinin from *Artemisia* plant material, alkaloids from *Catharanthus*, morphine and codeine from *Papaver* plant material, atropine and hyoscyamine from Solanacea plant material, galanthamine from Amaryllidaceae plants, antixoxidants from plant material, antibiotics from microorganisms, colorants from plants and microorganisms, flavonoids from plant materials, anthocyanins and carotenoids from flowers, an essential oil from a plant.

In another embodiment, specific polymeric compounds are extracted or dissolved, such as RNA, DNA, proteinic materials such as enzymes, toxins, vaccines, but excluding keratin, elastin and collagen, or polysaccharides, excluding chitin and chitosan. Preferred polysaccharides to be extracted or dissolved are lentinan, heparin, hyaluronan, alginate, agar, starch and inuline. The extracted materials can subsequently be isolated from the ionic liquid or deep eutectic solvent. It is also possible to use the solution as such for further processes. An example thereof of is the use of extracted enzymes, dissolved in the ionic liquid or eutectic solvent in enzymatic reactions. These reactions are then carried out in the said solvent or liquid. An example is the laccase reaction.

The invention is now elucidated on the basis of the following examples.

EXAMPLES

First the solubility of natural products, which are not soluble in water, was evaluated in a few selected natural deep eutectic solvents. Several flavonoids were chosen as the natural water-insoluble products, because they are one of the most abundant water-insoluble plant secondary metabolites. Up to now more than 500 flavonoids have been known. Most of these flavonoids occur in their glycosides forms (bounded to a sugar molecule) in plants. In spite of large abundance of flavonoids in plants, both the glycoside and the aglycone (non-sugar) part are not soluble in water. Thus, as a model research, the solubility of typical flavonoids including quercetin (aglycone), quercitrin (quercetin-3-O-rhamnoside) and rutin (quercetin-3-O-rhanmoglucoside), which have a very low water solubility, were tested in the naturally occurring deep eutectic solvents. The structure of these flavonoids are shown below.

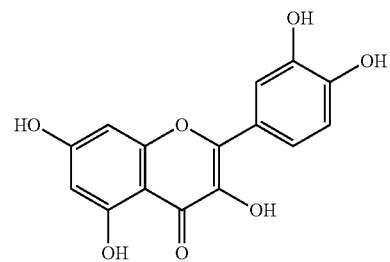

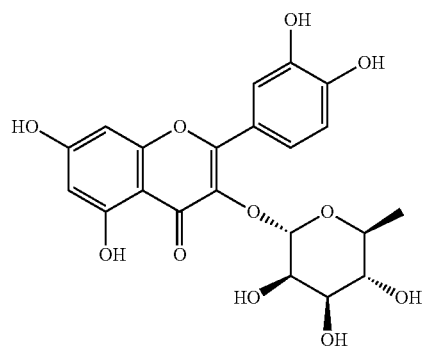

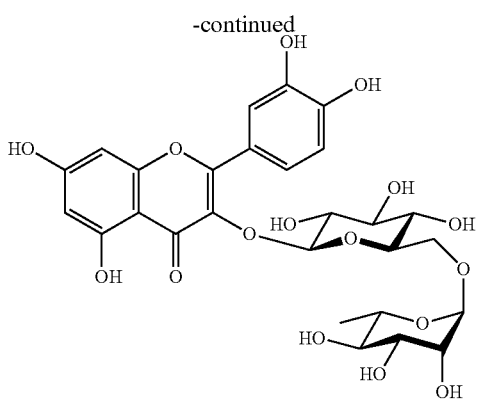

Structures of quercetin, quercitrin and rutin (left to right)

As shown in the table below the three flavonoids were found to be well dissolved in the natural deep eutectic solvents, with solubilities that are 2 to 4 orders of magnitude higher as compared to their solubilities in water.

TABLE 3

Solubility of flavonoids in several naturally occurring deep eutectic solvents

| Deep eutectic solvent | Solubility (mg/ml) | | |
|---|---|---|---|
|  | Quercetin | Quercitrin | Rutin |
| Sucrose + Choline chloride | 15.63 ± 0.57 | 12.68 ± 0.38 | 2.41 ± 0.18 |
| Glucose + Choline chloride | 21.56 ± 0.94 | 7.81 ± 0.20 | 4.78 ± 0.84 |
| Fructose + Choline chloride | 23.34 ± 2.54 | 11.25 ± 0.64 | 10.94 ± 1.70 |
| Water | 0.300 ± 0.002 | 0.159 ± 0.001 | <0.001 |

In order to confirm the solubility of flavonoids and the related anthocyanins, the flowers of red rose were extracted in the naturally occurring ionic liquids. It was observed that the red color metabolites are localized in the epidermis cells.

Extraction with the deep eutectic solvent fructose/glucose/malic acid (1:1:1 molar ratio) resulted in color removal from the flowers into the deep eutectic solvent phase. The structure of the flowers remained intact, with no breakdown of the natural structure.

The invention claimed is:

1. A process for extracting materials from a biological material, comprising:
    treating the biological material with an extractant comprising a deep eutectic solvent to produce a biological extract dissolved in said extractant, wherein the deep eutectic solvent comprises a first component and a second component, wherein the first component consists of at least one naturally occurring organic acid; and wherein the second component is selected from the group consisting of (i) at least one mono- or dimeric sugar or sugar alcohol selected from the group consisting of sucrose, glucose, fructose, lactose, maltose, galactose, raffinose, xylose, mannose, trehalose, sorbitol, erythritol, rhamnose, inositol, xylitol, ribitol, and adonitol, (ii) an amino acid selected from the group consisting of alanine, glutamic acid, glutamate, proline and serine, or (iii) 1,2-propanediol, or wherein the deep eutectic solvent comprises at least two sugars selected from the group consisting of glucose, fructose, sucrose and lactose; or wherein the deep eutectic solvent comprises (i) choline or betaine and (ii) said first component or said second component; and wherein the molar ratio of the components of the deep eutectic solvent is between 1:1 and 5:1; wherein the biological extract comprises a flavonoid or an anthocyanin; and wherein said biological material originates from a source selected from the group consisting of plants, insects, animals, and micro-organisms.

2. The process of claim 1, wherein the said naturally occurring organic acid is selected from the group consisting of: malic acid, maleic acid, citric acid, lactic acid, pyruvic acid, fumaric acid, succinic acid, acetic acid, aconitic acid, tartaric acid, ascorbic acid, malonic acid, oxalic acid, glucuronic acid, neuraminic acid and sialic acids.

3. The process of claim 1, wherein the deep eutectic solvent further comprises water.

4. The process of claim 1, wherein the deep eutectic solvent has a melting point below 25° C.

5. The process of claim 1, wherein the biological extract is recovered from said deep eutectic solvent.

6. The process of claim 1, wherein the deep eutectic solvent is selected from the group consisting of malic acid:β-alanine:water (1:1:3), proline:malic acid:water (1:1:3), fructose:glucose:sucrose:water (1:1:1:11), fructose:glucose:malic acid (1:1:1) and lactose:glucose:water (5:1:2).

7. The process of claim 1, wherein the flavonoid is rutin, quercetin or quercitrin.

8. A process for extracting materials from a biological material, comprising:
    treating the biological material with an extractant consisting of a deep eutectic solvent to produce a biological extract dissolved in said extractant, wherein the deep eutectic solvent comprises (i) alanine and malic acid, (ii) fructose and sucrose, (iii) fructose and glucose, (iv) proline and sucrose, (v) malic acid and glucose, (vi) malic acid and sucrose, (vii) citric acid and sucrose, (viii) lactose and glucose or (ix) glucose and; wherein the molar ratio of the components of the deep eutectic solvent is between 1:1 and 5:1; wherein the biological extract comprises galanthamine or paclitaxel; and wherein said biological material originates from a source selected from the group consisting of plants, insects, animals and micro-organisms.

* * * * *